US009521970B2

(12) United States Patent
Hoppe et al.

(10) Patent No.: US 9,521,970 B2
(45) Date of Patent: Dec. 20, 2016

(54) MONITORING DEVICE FOR ATTACHMENT TO A SURFACE OF A SUBJECT

(75) Inventors: Karsten Hoppe, Copenhagen Ø (DK); Jakob Janting, Lyngby (DK)

(73) Assignee: BIOTELEMETRY TECHNOLOGY APS, Hellerup (DK)

(*) Notice: Subject to any disclaimer, the term of this patent is extended or adjusted under 35 U.S.C. 154(b) by 1214 days.

(21) Appl. No.: 13/518,780

(22) PCT Filed: Dec. 22, 2010

(86) PCT No.: PCT/EP2010/070539
§ 371 (c)(1),
(2), (4) Date: Sep. 10, 2012

(87) PCT Pub. No.: WO2011/076871
PCT Pub. Date: Jun. 30, 2011

(65) Prior Publication Data
US 2012/0330126 A1    Dec. 27, 2012

(30) Foreign Application Priority Data
Dec. 23, 2009    (EP) .................................... 09180528

(51) Int. Cl.
*A61B 6/00*    (2006.01)
*A61B 5/00*    (2006.01)
(Continued)

(52) U.S. Cl.
CPC ......... *A61B 5/14551* (2013.01); *A61B 5/0002* (2013.01); *A61B 5/02438* (2013.01);
(Continued)

(58) Field of Classification Search
None
See application file for complete search history.

(56) References Cited

U.S. PATENT DOCUMENTS 5,054,488 A    10/1991 Muz
5,458,124 A    10/1995 Stanko et al.
(Continued)

FOREIGN PATENT DOCUMENTS

DE    10 2005 038 148 A1    2/2007
WO    WO-99/59465    11/1999
(Continued)

OTHER PUBLICATIONS

Rasmus G. Haahr et al., "A Novel Photodiode for Reflectance Pulse Oximetry in low-power applications", *Proceedings of the 29th Annual International Conference of the IEEE EMBS*, Aug. 23-26, 2007, pp. 2350-2353.
(Continued)

*Primary Examiner* — William Thomson
*Assistant Examiner* — Marie Archer
(74) *Attorney, Agent, or Firm* — Ropes & Gray LLP

(57) ABSTRACT

The invention provides a monitoring device (1) for attachment to a surface of a subject. The device comprises a data collector (2) and a processor (3) as two separate parts which can be detachably joined such that physiological signals which are detected by the data collector can be transferred to the processor for signal processing and provision of monitoring data. At least one of the data collector and the processor comprises a transducer which can convert the physiological signal to a data signal which can be processed electronically. The data collector is adapted for adhesive contact with a skin surface, and may comprise an adapter (6) for the detachable attachment of the processor.

14 Claims, 7 Drawing Sheets

(51) Int. Cl.
*A61B 5/1455* (2006.01)
*F16B 2/20* (2006.01)
*A61B 5/024* (2006.01)
*F16B 2/00* (2006.01)
*A61B 5/01* (2006.01)
*A61B 5/0432* (2006.01)
*A61B 5/0476* (2006.01)
*A61B 5/0488* (2006.01)
*A61B 5/08* (2006.01)

(52) U.S. Cl.
CPC ............. *A61B 5/6833* (2013.01); *F16B 2/20* (2013.01); *A61B 5/01* (2013.01); *A61B 5/0432* (2013.01); *A61B 5/0476* (2013.01); *A61B 5/0488* (2013.01); *A61B 5/0816* (2013.01); *A61B 2560/0276* (2013.01); *A61B 2560/0412* (2013.01); *A61B 2560/0443* (2013.01); *A61B 2562/08* (2013.01); *A61B 2562/146* (2013.01); *A61B 2562/247* (2013.01)

(56) References Cited

U.S. PATENT DOCUMENTS

| | | | |
|---|---|---|---|
| 6,317,630 B1* | 11/2001 | Gross | A61N 1/30 604/20 |
| 6,736,759 B1* | 5/2004 | Stubbs | A63B 22/00 482/5 |
| 7,606,608 B2* | 10/2009 | Blank | A61B 5/14532 600/344 |
| 2002/0077673 A1* | 6/2002 | Penner | A61B 5/00 607/60 |
| 2003/0149349 A1* | 8/2003 | Jensen | A61B 5/02055 600/372 |
| 2004/0077954 A1 | 4/2004 | Oakley et al. | |
| 2004/0100376 A1* | 5/2004 | Lye | A61B 5/411 340/539.12 |
| 2004/0247236 A1* | 12/2004 | Yoshimura | G02B 6/12002 385/16 |
| 2005/0075846 A1* | 4/2005 | Kim | G01H 9/004 703/1 |
| 2007/0012112 A1* | 1/2007 | Kim | G01H 9/004 73/594 |
| 2007/0032721 A1* | 2/2007 | Crane | A61B 5/0059 600/407 |
| 2007/0100219 A1 | 5/2007 | Sweitzer et al. | |
| 2007/0185393 A1* | 8/2007 | Zhou | A61B 5/0402 600/323 |
| 2007/0219437 A1* | 9/2007 | Schurman | A61B 5/0066 600/316 |
| 2008/0091090 A1 | 4/2008 | Guillory et al. | |
| 2008/0275327 A1* | 11/2008 | Faarbaek | A61B 5/0002 600/382 |
| 2009/0088823 A1* | 4/2009 | Barak | A61B 18/203 607/89 |
| 2010/0081913 A1* | 4/2010 | Cross | A61B 5/04085 600/386 |
| 2011/0098609 A1* | 4/2011 | Hall | A61N 7/02 601/2 |

FOREIGN PATENT DOCUMENTS

| | | |
|---|---|---|
| WO | WO-03/065926 A2 | 8/2003 |
| WO | WO-2006/094513 A2 | 9/2006 |
| WO | WO-2006/110488 A2 | 10/2006 |
| WO | WO-2007/063436 A1 | 6/2007 |
| WO | WO-2008/057884 A2 | 5/2008 |
| WO | WO-2008/068695 A1 | 6/2008 |
| WO | WO-2009/036306 A1 | 3/2009 |
| WO | WO-2009/124076 A1 | 10/2009 |

OTHER PUBLICATIONS

Rasmus G. Haahr et al., "A Wearable "Electronic Patch" for Wireless Continuous Monitoring of Chronically Diseased Patients", *Proceedings of the 5th International Workshop on Wearable and Implantable Body Sensor Networks, in conjunction with the 5th International Summer School and Symposium on Medical Devices and Biosensors*, Jun. 1-3, 2008, pp. 66-70.

Huafeng Ding et al., "Refractive indices of human skin tissues at eight wavelengths and estimated dispersion relations between 300 and 1600 nm", *Phys. Med. Biol.*, Mar. 1, 2006, pp. 1479-1489, vol. 51.

G.J. Tearney et al., "Determination of the refractive index of highly scattering human tissue by optical coherence tomography", *Optics Letters*, Nov. 1, 1995, pp. 2258-2260, vol. 20, No. 21.

\* cited by examiner

MONITORING DEVICE FOR ATTACHMENT TO A SURFACE OF A SUBJECT

INTRODUCTION

The present invention relates a monitoring device suitable for monitoring an individual. In particular, the invention relates to a device which is adhesively attached to the skin of the individual and which comprises a processor which can process a physiological signal which is received from the individual.

BACKGROUND OF THE INVENTION

WO 2006094513 discloses a micro electronic system predominantly for monitoring physiological or neurological conditions. The system is embedded in a three-dimensional adhesive device which can be attached to the skin of a mammal. The microelectronic system uses wireless communication and it is useful for measuring ECG (Electro CardioGraphy), EMG (Electro MyoGraphy), EEG (Electro EncephaloGraphy), blood glucose, pulse, blood pressure, pH, and oxygen.

WO 03/065926 discloses a wearable biomonitor with a flexible and thin integrated circuit. The disclosure includes ways to achieve high comfort of wear by using a thin layer adhesive or pads of adhesive for fixation to the skin.

U.S. Pat. No. 5,054,488 discloses an opto-electronic sensor for producing electrical signals representative of a physiological condition. The sensors may be attached to the body by a double-sided pressure sensitive adhesive on a polyester lining.

Rasmus G. Haahr et al. Proceedings of the 5th International Workshop on Wearable and Implantable Body Sensor Networks, in conjunction with The 5th International Summer School and Symposium on Medical Devices and Biosensors, The Chinese University of Hong Kong, HKSAR, China. Jun. 1-3, 2008, relates to a wearable for Wireless continuous monitoring of physiological signals in chronically diseased patients.

Rasmus G. Haahr et al. Proceedings of the 29th Annual International Conference of the IEEE EMBS Cité Internationale, Lyon, France Aug. 23-26, 2007 describes a photodiode for reflectance pulse oximetry in wireless applications of a patch.

SUMMARY OF THE INVENTION

It is an object of embodiments of the invention to provide an improved sensor for monitoring of an individual.

Accordingly, the invention, in a first aspect, relates to a monitoring device suitable for attachment to a surface of a subject, the device comprising a data collector and a processor, the data collector having a lower surface adapted for adhesive contact with a skin surface of the subject and adapted for receiving a physiological signal from the surface, the data collector comprising a transmission structure for transmitting a monitoring signal which represents the physiological signal to the processor, and the processor being detachably attachable to an upper surface of the data collector and comprising a connection structure which, upon attachment, connects to the transmission structure for receiving the monitoring signal from the data collector, wherein the processor comprises an electronic circuit for processing the monitoring signal to provide monitoring data which relates to a physiological state of the subject, wherein at least one of the data collector and the processor comprises a transducer which can convert the physiological signal to a data signal which can be processed electronically.

Due to the two separate components being detachably attachable to each other, it becomes possible to use the processor with different data collectors. As an example, data collectors with different size, shape or transmission structures could be provided for use with one and the same processor. In another example, the user may reuse the processor after having changed the data collector, e.g. after sport, bathing, or after other activities which may render the data collector wet, dirty or otherwise worn out.

In the following, the two separate components will be described in details and subsequently, the interface between the two components and additional functions will be described.

The main function of the data collector is to adhere to the body of the subject, to recognize physiologic signals there from, and to transmit the monitoring signals which represents the physiologic signal to the processor. The monitoring signal may be the physiologic signal itself or the data collector may comprise a transducer for converting a physiological signal into another form, typically a form which is easier to transfer to the processor and/or a form which is more easily processed by the processor. As it will be described in further details in a separate paragraph, the transducer may form part of the data collector, the processor or both.

Examples of physiological signals relevant in connection with the invention include an electrical or optical signal such as sternum PPG, a pressure signal, a thermal signal or any other signal derivable from the body of the subject. Such a signal may be significant for a physiological condition of the subject and in particular for vital parameters where failure will lead to death, e.g. significant for arterial oxygen saturation ($SpO_2$) which can be found by pulse oximetry, or significant for heart beat rate which may be found in various ways including pulse oximetry etc, or significant for respiration rate which again can be found e.g. by pulse oximetry and oxygen saturation.

In some embodiments in the system according to the present invention the device comprises at least one sensor and optionally several different sensors. The sensor(s) may be configured for measuring one or more physiological signal selected from electrocardiography (ECG), electromyography (EMG) electroencephalography (EEG), galvanic skin response (GSR), phonocardiogram (PCG), arterial oxygen saturation (Sp02), muscle activity, emotions, arterial saturation of carbon monoxide (SpCO) and blood carbon dioxide (CO2), blood pressure (BP), respiration, such as respiration frequency (RF) and/or respiration volume (RV), heart rate (HR), pulse, bioimpedance, and/or rhythm, heart sounds, respiratory sounds, blood pressure, posture, wake/sleep, orthopnea, heat flux, patient activity, snoring sound or other sounds of the subject, and temperature, such as skin temperature (ST), and/or core body temperature.

In general, the physiological signal will be recognized and picked up from the individual by a structure which in the following will be referred to as "the detecting component". This component can e.g. include electrodes (polar, bipolar), pressure sensors, needles with electrodes, accelerometers, photo detectors, microphones, ion specific field effect transistors (ISFET), a NTC (negative temperature coefficient) resistors, band gap detectors, ion membranes, enzyme reactors or condensers etc. In particular, the device may comprise components for non-invasive capturing of the physiological signal, e.g. electrodes or optic recognition means.

The component could, however, also be for invasive capturing of the physiological signal, e.g. in the form of a needle for taking fluid samples, or a needle containing an electrode for subcutaneous capturing of an electrical physiological signal.

In addition to the component for capturing of the physiological signal, or as an alternative to the component for capturing of the physiological signal, the data collector may comprise an actuator, i.e. a component which converts energy from one form, typically electrical energy, to another body sensible form, which can act on the body of the individual. Examples of such actuator components are electrodes, e.g. for neural- or neuro-stimulation, pumps, injection needles, light emission diodes (LED) or other emitters of electromagnetic radiation, pressure wave generators such as loudspeakers, current generators, or chemical synthesizers. Accordingly, the data collector may be designed for two way communication of signals to and from the individual.

The data collector may be designed for a specific purpose, e.g. for collecting electrical signals from a muscle etc. According to the specific intended use, the data collector may have a shape which matches a specific location on the body of the subject. Additionally, the detecting component and the power supply which is optionally included in the data collector could be designed for the specific signal in question.

To ensure correct operation together with the processor, the data collector may include identification means which identifies the type of data collector towards the processor. In this way, the processor may automatically adapt to the kind of signals which are monitored, adapt suitable power schemes for optimal power consumption the specific physiological signal in question etc.

The data collector may further include identification means which identifies the user as such, which identifies a disease, which identifies a physical condition to be monitored, or which identifies other aspects of the user towards the processor. As an example, the data collector may be made specifically for a physical condition, or for a particular user. When this dedicated user attaches a processor to the correspondingly dedicated data collector, the user, condition etc. is identified by the processor which can act in a suitable manner, e.g. by processing the signal, by using a specific power scheme, by using a specific sampling frequency or by matching in other ways, the user, the condition or other identified prerequisite of the monitoring in question.

Accordingly, the monitoring device may comprise scheme memory means with specific data schemes corresponding to a mode of operation, and the identification means may be adapted to select from these schemes, one mode of operation matching the identification. The scheme memory means may form part of the data collector, the data processor or both.

The data collector may also include identification means which identifies a recipient who is intended to receive the monitored data, e.g. an e-mail address or web address of a medical practitioner etc.

The data collector may include identification means which identifies a specific encryption for encrypting the data. When the processor reads the identification, it may become capable of encrypting the data such that only those having corresponding identification or encryption schemes available can deduct useful information from the processor. This feature may highly increase the safety of the device, and it may effectively prevent unauthorized people from getting personal sensitive information. The feature may furthermore ensure that the user only returns to an authorized medical practitioner to have the data analyzed or evaluated.

As an example, a hospital may supply a user with data collectors for a specific purpose. The user may use a standard processor in combination with the received data collectors, and after use, the data could only be evaluated by the hospital who initially handed out the data collectors since only they are in possession of the matching encryption/decryption capabilities.

The data collector may include identification means which identifies an expected lifetime of the data collector. This feature may effectively prevent use of data collectors where the battery or other features have become too old to function correctly.

The data collector may include a data storage, e.g. an e-prom or similar device for storage of electronic data. The data storage may in particular be accessible by the processor such that the monitored data can be written on the data storage of the data collector. In this way the user may return the data collectors, e.g. by traditional mail, to the medical practitioner who is capable of analyzing the monitored signal or generated data.

The data collector may generally include two main components, i.e. a base and an adapter. The base may be made from a flexible tape or patch with an adhesive on at least the lower surface which is to face towards the subject and which is therefore intended to bond the device to the subject. The adapter forms the interface for the processer and it may further comprise various structures, e.g. a power structure for powering the processor, a transducer and/or the transmission structure for transmitting signals to the processor. Compared with the base, the adapter may be made from a more rigid and less elastically deformable material.

The lower surface or base may comprise a gel, e.g. a hydrogel with adhesive properties. The hydrogel may or may not be electrically conductive. Different forms or formulations of the hydrogel with different properties may be used within the same system or device.

Examples of suitable hydrogels may be obtained from Axelgaard Manufacturing Co., Ltd: http://www.axelgaard.com/home.htm or its subdivision AmGel Technologies; http://www.amgel.com/index.html.

The adhesive or gel may form a transmission passage for the physiological signal from the individual on which the device is attached to the detecting component.

In particular, the passage may be a non-interrupted passage from the place of contact with the individual, e.g. the surface of the skin, to the detecting component.

The adhesive may form a transmission passage for the physiological signal from the individual to the detecting component. In particular, the passage may be a non-interrupted passage from the place of contact with the individual, e.g. the surface of the skin, to the detecting component.

In case of detection of e.g. optic or acoustic physiologic signals, such a non-interrupted passage in one and the same material, namely the adhesive (such as a gel), provides for a minimal loss of signal strength and quality, such as by preventing reflection, scattering, and refraction in an interface between materials with different properties such as refractive indices.

The lower surface may comprise an adhesive or gel which amends the physiological signal, e.g. a gel which modifies an optical signal, filters an electrical signal or dampens an acoustic signal.

In particular, it may be an advantage to use an adhesive, e.g. in form of a hydrogel or similar material with properties ranging from soft and weak jelly-like to hard and tough yet deformable, and it may further be an advantage to use a material with a refractive index in the range of 1.01-1.7 e.g. 1.30-1.45, such as 1.34-1.42. In this way, the index becomes close to that of average skin whereby reflection of the physiological signal, be that an acoustic or optic signal, can be prevented or at least reduced.

In one embodiment, the base comprises both an adhesive lower surface and an adhesive upper surface. In this case, the adapter may be fixed to the base by the adhesive upper surface of the base. In a simple embodiment, the adhesive is electrically conductive, e.g. with a volume resistance in the range of 500-1500 ohm*cm and therefore serves both to conduct electricity and to affix the data collector to the individual.

In other embodiments, the adhesive and detecting component are separate components. In this case, the adhesive may e.g. encapsulate one or more detecting components on the lower surface of the data collector.

The adapter may project in an upwards direction from the upper surface. An anchoring structure formed on the adapter may cooperate with a gripping structure on the processor for the detachable attachment of the processor to the data collector.

In one embodiment, the base forms an electrically conductive layer towards the subject and the adapter comprises the transmission structure in the form of electrically conductive paths in a body of a non-conductive material, e.g. pins or wires which are carried by a body of a non-conductive material. Herein, non-conductive should be understood as "having an electrical conductivity much lower than that of the conductive paths". In this way, the paths form a transmission structure adapted to transfer electrical signals. Electrical connectivity with the processor may also be obtained by use of conductive brushes etc. or by use of zebra type elastomeric connectors like those which can be purchased at the Z-axis Connector company, c.f. http://www.zaxisconnector.com or from Fujipoly, c.f. http://www.fujipoly.com. In zebra wire interconnections, gold wires are at a surface of silicone rubber and ensure good electrical contact while also providing a counter force for snap locking assembly of the data collector and processor.

To increase flexibility of the device, the transmitters could include a number of conductive pins which are individually suspended in a body, e.g. such that the pins are movable relative to each other in the body. The body may e.g. be made from an electrically isolating material, e.g. such that the body shields against noise and thereby prevents electrical interference etc.

The electrical conductivity through the base can be provided e.g. by use of a liquid and electrically conductive gel encapsulated in a thin patch. In this way, the base will easily adapt to the body shape of the subject and the conductivity through the base is not influenced by bending or stretching of the base.

In an alternative embodiment, or in combination with the mentioned electrical paths from the lower surface to the processor, the data collector may form a transmission structure for transfer of optical signals from the subject to the processor. Such a structure may include fiber optics or simply a passage for light or similar electro magnetic radiation from the lower surface to the processor. It may further include a CCD processor or similar electronic means for converting an optical signal into an electrical signal.

Generally, the transmission structure may combine different signals, e.g. as separate signals, or different signals may be converted e.g. into an optical or electrical signal which is transmitted to the processor.

It may be an advantage to include in the data collector, a power source for the processor and other power consumers of the device. In this way, the power source may be optimized to a specific purpose and for a specific physiologic signal. The power source could be a traditional battery.

To ensure good connectivity between the battery in the data collector and the processor, the battery may be pressed in an upwards direction away from the lower surface. When the processor is attached to the data collector, the battery may thereby be pressed against a lower surface of the processor.

To press the battery against the processor, the battery may be housed in a body which includes spring force means which provides a spring force against a lower surface of the battery and thereby raises the battery towards the processor. The body may e.g. form a cup shape with an upwardly curved bottom part which is elastically deformable downwards and which seeks back in an upwards direction upon deformation downwardly. Accordingly, the body forms a seat for the battery, and the seat may comprise additional features for securing the battery in place, for providing conductivity between the poles of the battery and corresponding poles on the processor etc.

The gripping structure could be adapted to destroy the anchoring structure upon detachment of the data collector from the processor. In this way, it is ensured that the data collector is not reused several times, and the data collection quality may thereby be better ensured.

The anchoring structure and the body in which the battery is seated could be made in one part, and this same part could also hold electrical conductive pins or in other ways form the mentioned transmission structure. For this purpose, this single part may included a shielding component which protects against radio interference etc and which thereby reduces or prevents induction of a current in the transmission structure, in case it includes electrically conductive paths etc.

Herein, the data which is received by the processor is described as "a data signal". The data signal could be the physiological signal itself, e.g. an electrical impulse transmitted by a muscle etc. In this case the data signal can be transmitted directly to the electronic circuit by an electrically conductive transmission structure.

The monitoring device may comprise filter means for modifying the data signal. Such modification may include amplification, noise reduction, data comparing or any similar form of data analyzing. The filter means may be included in the data collector, in the data processor, or in both. In particular, it may form part of the transducer.

Alternatively, the data signal could represent a physiological signal which is transformed for electrical or optical transmission from the skin of the individual to the electronic circuit. This could be the case e.g. if the physiological signal is a temperature of the skin, a skin color, a reflectance etc. In such cases, the color, temperature etc is typically transformed into an electrical or optical signal receivable by the electronic circuit. The transformation of the physiological signal to a data signal, or any later transformation of the data signal into a more processor friendly signal, is carried out by a transducer. In the illustrated embodiment, the transducer forms part of the electronic circuit or it forms part of software executed in the electronic circuit.

The electrical circuit may comprise one or more application specific integrated circuits (ASIC), electrical system or subsystem, such as, but not limited to, printed circuit boards (PCB), flexible printed circuit boards (FPCB), thick film, thin film, or ceramic technologies or the system or its components may be separately encapsulated.

To communicate the processed data signal e.g. with an external computer system, with an alarm central or similar surveillance or monitoring system, the device may comprise wireless communication abilities of well known kind. This may include Radio Frequency Identification (RFID) tags which are commercially available in various sizes, ranges and functionality. When the RFID reader applies the appropriate field (e.g. an inductive field) the basic RFID tag return a bit sequence. The sequence is programmed prior to use. RFID range varies from 1 cm to app. 2 meter for passive tags (no power source included) to over 100 meters for active tags (power source included). More sophisticated RFID tags available have storage components where data can be read or stored.

The wireless communication may form part of the electronic circuit, or optionally, it may form part of the data collector. As an example, the electronic circuit or the data collector may include an RF chip and a coil. Suitable forms of the RFID tag is a RFID tag encapsulated in a glass housing, a RFID tag encapsulated in plastic/epoxy (typically pill shaped), a flat RFID tag with coil and a RF chip laminated between 2 polyimide layers, or a flat RFID tag with large coil antenna with few turns printed on or in the adhesive body and with the RF chip interconnected to the antenna without any further protection/encapsulation.

The wireless communication, in particular in form of a RFID tag, may, when forming part of the data collector, be used to identify either the individual, or the type of data collector towards the processor. As an example, the identification may relate to the type of physiological signal to which the data collector pertains, it may relate to the age of the data collector or the duration where the data collector was attached to the skin of the individual, the identity of the individual or other characteristics.

In one embodiment, the identification tag is embedded in the adhesive foil 8.

The communication between the device and other devices may be coordinated in a FFD device, e.g. forming part of the electronic circuit. The FFD devices may function at any topology and be the coordinator of the Network, or it may be a coordinator that can talk to any other device. A RFD device is limited to star topology, it cannot become a network coordinator, it talks only to a network coordinator and has very simple implementation. FFDs may be a dedicated network coordinator acting as communication Hub, gateway or router within the Body Area Network (BAN) and handling communication with external unit(s). A communication Hub or gateway may have large storage capacity and store data from the sensor network, and when in proximity with external unit or when otherwise appropriate wirelessly transmit these data.

In particular for monitoring behavior of the individual, or for making combinations between physical activity and other physiological signals, the device may comprise a GPS element, e.g. embedded in the electronic circuit. The system may e.g. log data related to the position, speed or acceleration of the individual or the limp to which the device is attached.

The electronic circuit could form a gateway comprising storage and communication components, a CPU and a battery encapsulated in plastic and working as a dedicated network coordinator for transmission of data to a central unit (CU).

The electronic circuit which forms part of the processor could be located and protected in a capsule, e.g. a capsule made in one piece, e.g. from a single sheet of metal or made from plastic.

The capsule may form an opening which has a size and shape enabling it to receive at least a portion of the adapter. To protect against intrusion of dirt and moist etc, the adapter and opening may have shapes which matches so well that a gap of at most 1 mm and preferably of less than 0.5 mm between the processor and data collector is formed when the two parts are assembled.

For ensuring a tight assembly, the adapter may form a plane ledge around and upwards projecting tower and the processor may correspondingly form a plane ledge extending circumferentially about the opening. Furthermore, the dimensions may be selected such that the ledge of the processor and the ledge of the data collector can come into contact with each other, or at least become so close that at most 1 mm. or at most 0.5 mm between the ledges exist when the tower is inserted in the opening and the gripping and anchoring structures are engaged.

The opening and tower may advantageously be circular such that the processor can rotate around the tower, and to make electrical connectivity between the processor and data collector independent on a rotational orientation of one part relative to the other part, the connectors forming part of the transmission structure may be arranged symmetrically around a center of the circular opening and tower.

The transducer may, as mentioned already, form part of the processor and/or of the data collector. Additionally, the transducer may form a separate component which is attachable to on or both of the processor and data collector, or which may be inserted between the processor and data collector before the assembly of these two components.

The transducer is designed to convert energy from one form to another. The transducer is typically, but not necessarily, the sensor or sensing part of the microelectronic sensing system. A transducer may thus be able to convert for example a physical input and the transducer will usually but not necessarily convert this energy into electrical form to be interpreted by the CPU etc.

Examples of the physical input a transducer may convert is acceleration, chemical/gas, flow, humidity, inertia, capacitance, conductance, conductivity, current, impedance, inductance, pH, resistance, voltage, photo detection, light, magnetism, pressure, angular, linear position, velocity, temperature, sound and mechanical force.

In one embodiment, the transducer is simply constituted by the transmission structure in combination with electrodes in contact with the skin of the individual or in combination with an electrically conductive adhesive.

The processor and/or the data collector may comprise processing means and corresponding program code which renders the device suitable for various monitoring tasks.

As mentioned with regards to the processor and data collector, the signals and/or monitoring data may be encrypted. For this purpose, the software may include programs for performing such encryption.

In a second aspect, the invention provides a method of monitoring data based on physiological signals received from a subject by use of a device as already described.

The method comprises attaching a data collector capable of detecting physiological signals to a surface of the subject and using a separate processor which is attached to the data collector for processing the detected signals and to provide monitoring data which relates to a physiological state of the subject, wherein at least one of the data collector and the processor comprises a transducer which can convert the physiological signal to a data signal which can be processed electronically.

The subject or the data collector may be identified by the processor by use of an identification tag forming part of the data collector.

DETAILED DESCRIPTION OF THE DRAWINGS

Figure 1:
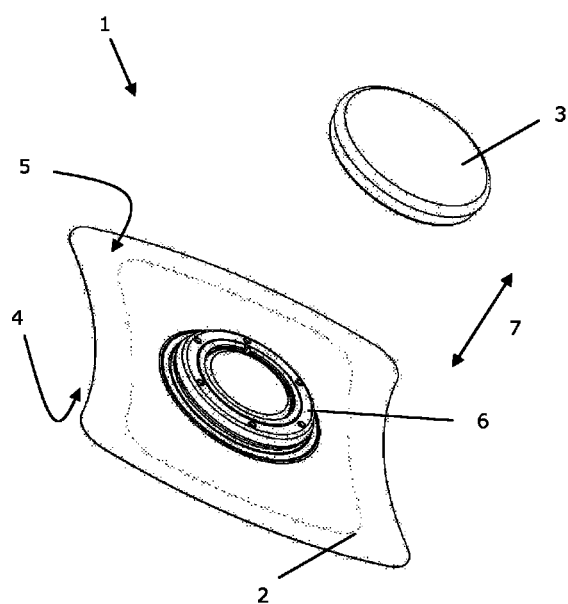
FIG. 1 illustrates a monitoring device according to the invention.

FIG. 1 illustrates a monitoring device 1 with a data collector 2 and a processor 3. The data collector has a lower surface 4 provided with a body compatible adhesive, e.g. a hydrogel based adhesive for attachment of the lower surface to the skin of an individual. The lower surface is electrically conductive such that a physiological signal can be received though the lower surface. The physiological signal could e.g. be an electrical signal from a muscle, a color signal or similar optical signal received by a photo sensor etc.

Figure 5:
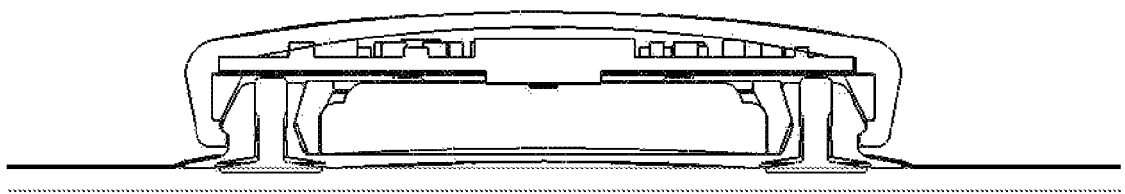

The data collector comprises a base forming the lower surface 4 and an opposite upper surface 5. The data collector further comprises an adapter 6 projecting in an upwards direction, indicated by the arrow 7 from the upper surface. The adapter forms an anchoring structure cooperating with a gripping structure on the processor and thereby enables detachable attachment of the processor to the data collector. The anchoring and gripping structures are illustrated in FIG. 5.

Figure 2:
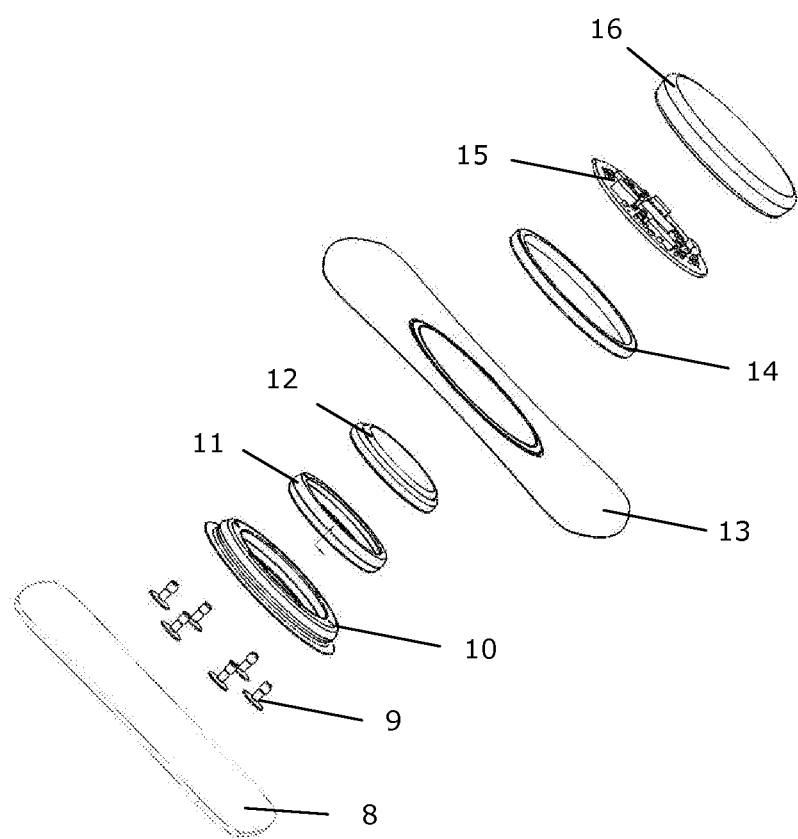
FIGS. 2 and 3 illustrate exploded views of the monitoring device.

FIG. 2 illustrates an exploded view of the monitoring device. From the bottom towards the top, the device comprises the following elements:
8. a foil with double sided adhesive;
9. a group of transmitters including in this case 6 individual transmitters for transmitting an electrical signal from the foil.
10. A body element.
11. An electrically conductive ring or bushing inserted in the body 10 and encircling a battery.
12. A battery which is encircled by the ring 11 such that the ring conducts one of the two phases of the battery.
13. A cover foil which is attached adhesively to an upper surface of the foil 8. The cover foil 13 is preferably made from a soft, smooth, and bendable material, e.g. from a woven or non woven fabric.
14. A fixing ring for holding the electronic circuit fixed in a capsule and comprising a gripping structure for holding a cooperating anchoring structure provided on the data collector.
15. An electronic circuit capable of processing the data.
16. A capsule housing the electronic circuit.

The foil 8 may have a proximal side facing towards the individual to be adhered to the skin of the individual. The proximal side is provided with a first adhesive layer and a release liner can be arranged thereon (not shown) for protecting the first adhesive layer until use. The first adhesive layer may e.g. be a hydrocolloid skin protective adhesive manufactured by 3M.

A second adhesive layer can be provided on the opposite, distal, side of the foil. The purpose of the second adhesive layer is to fix the body element 10 solidly to the foil 8. Accordingly, the second adhesive layer may provide a much stronger bonding than the first adhesive layer.

The cover foil 13 is attached to the second adhesive layer around the body element 10 to provide a smooth and appealing appearance and optionally to provide specific characteristics of the device with respect to bending stiffness, durability, or rigidity. Accordingly, the cover foil 13 may have characteristics regarding stiffness, durability, and/or rigidity which are different from that of the foil.

The body element 10 may be formed in one piece from a non-conductive material, e.g. from a plastic material, or formed from a magnetically shielding material such as a plastic material with embedded metal fibers. The bending stiffness, rigidity, and/or the ability of the body element 10 not to elastically deform may be superior compared to that of the foil 8 and cover foil 13.

The body element 10 houses the battery 12 which delivers the electrical power to the processor but it forms part of the data collector such that a new battery can be provided with every new data collector. Accordingly, the battery may e.g. be of the kind unsuitable for recharging. Many battery sizes and cell casing exist, including standard cylindrical cells, multi-cell batteries, coin cells, pouch cells and thin film batteries. Any of these could become suitable for the device depending on the need for battery capacity and the design of the device.

Figure 6:
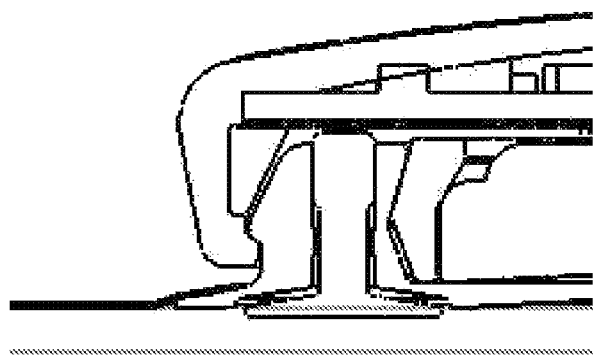

The body element 10 forms a tower which can be received in the opening in the processor. The body element further forms an anchoring structure to be gripped by the gripping structure of the processor, c.f. FIGS. 5 and 6.

The data collector comprises a transmission structure consisting in this case of a plurality of individual transmitters 9 which can transmit an electrical data signal from the lower surface to the processor. The transmitters 9 are arranged circumferentially around the body element 10 and thus around the battery 12. The body element 10 is made from a non-conductive material and therefore effectively isolates the transmitters from each other. The body 10 may further be molded with a shielding structure which reduces induction of electrical noise in the transmitters 9.

Each of the illustrated six transmitters is individually and movably suspended in the body element 10 which thereby electrically isolates the transmitter from other transmitters and from the battery 12.

The processor includes the fixing ring 14, the electronic circuit 15, and the capsule 16.

The processor generally processes the received data signal and to do so, it consumes electrical power obtained from a power source.

Further, the processor may be adapted to store the received data signal until the time where it is being processed, to store the result of the processing of the data signal, and to store software necessary for the transformation of the received data signal. For this purpose, a storage component may form part of the electronic circuit for storage of the embedded system software and/or storage of data acquired during operation of the device. The storage component may be a part of the CPU, a component of its own or an exchangeable storage device such as FLASH RAM that can be removed and exchanged.

Figure 3:
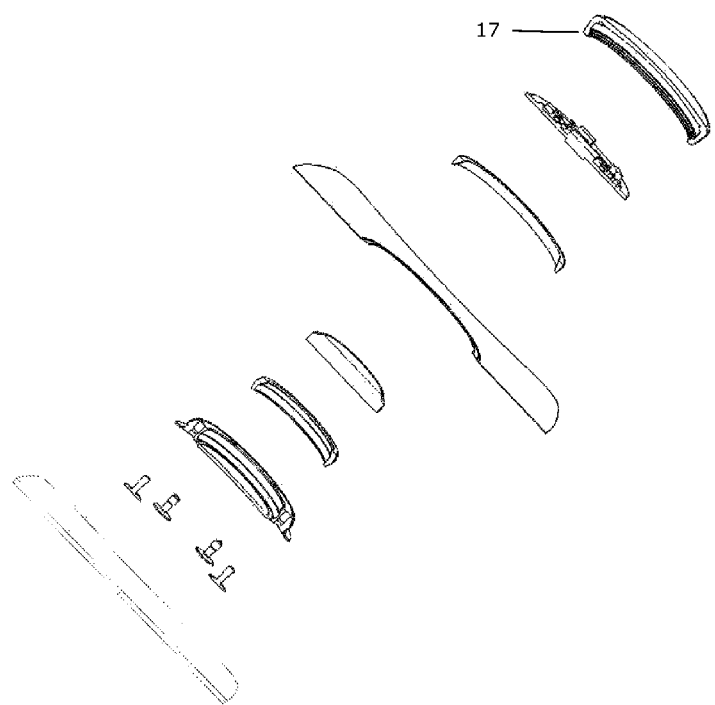

FIG. 3 illustrates a side view of the device which is illustrated in FIG. 2. In this view, it is clear that the capsule 16, and thus the processor 14, 15, 16 forms a plane ledge 17 extending circumferentially about the opening. The capsule is made in one piece from a blank of metal.

Figure 4:
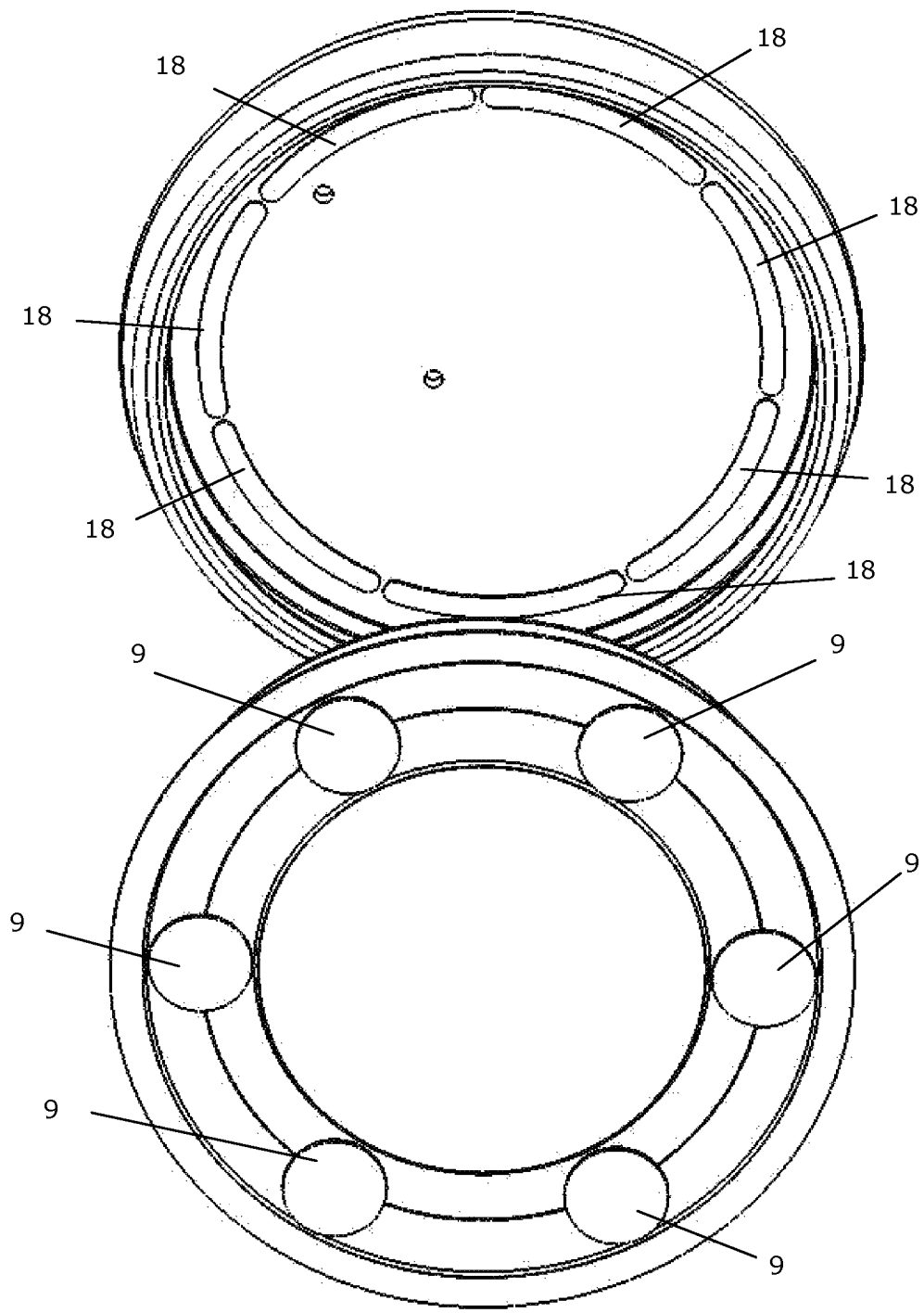
FIGS. 4-6 illustrate details of the monitoring device.

FIG. 4 illustrates the capsule 16, the electronic circuit 15, and the body element 10 including the transmitters 9 seen from below. In this view, it is clearly visible that the opening in the capsule 16 is circular. The connection structure and transmission structure are adapted for transmission of the data signal from the data collector to the processor independently on a rotational orientation of the processor relative to the data collector. This feature is provided by the 6 transmitters 9 which cooperate with the 7 conductive fields 18 which constitute the connection structure, and which each has a length which provides contact between each transmitter and an individual one of the fields 18 irrespective of the mutual orientation of the connection structure and transmission structure.

FIGS. 5 and 6 illustrate a cross section of a gripping structure of the processor which is adapted to destroy an anchoring structure of the data collector upon detachment of the data collector from the processor. This function will guarantee one-time-use of the data collector and thus improve the reliability of the device.

Figure 7:
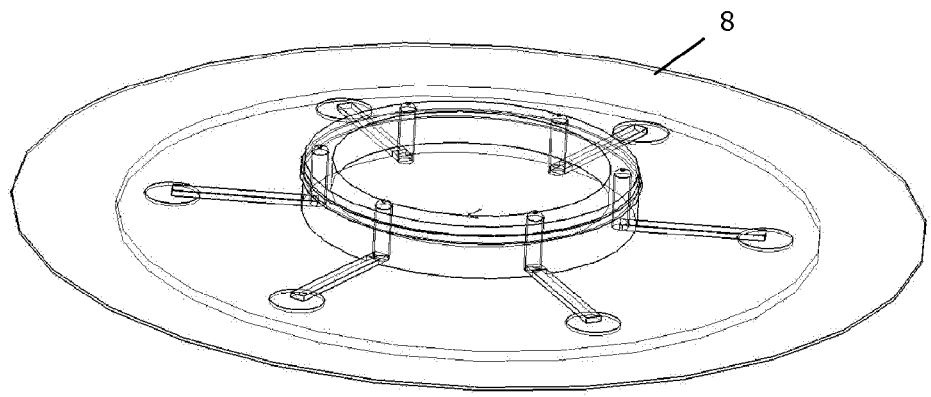
FIG. 7 illustrates a 3D MID on a foil.

FIG. 7 illustrates the transmission structure made with 3D MID which allows integration of mechanical and electrical functions in a moulded part. In a first injection cycle, moulding material is injected onto the foil 8 to form the body element 10 directly on the foil. In this stage the body element 10 is moulded with channels which are filled with an electrically conductive polymer in a second injection cycle. In the second injection cycle, the conductive polymer is injected into the channels and out onto the foil 8 on those locations where there is contact down through the foil into the conductive gel and/or conductive adhesive which comes in contact with the skin of the subject.

EXAMPLE

The following is an example of further details which may be included in a device according to the invention.

Figure 8:
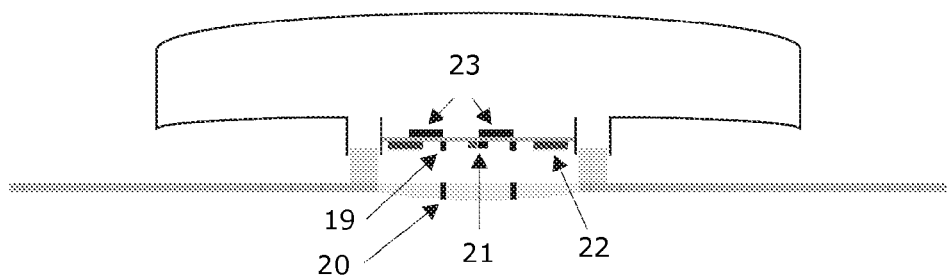

FIG. 8: The fig. illustrates a possible integration of the optical system and components in the monitoring device. The optical components are integrated as a part of the Processor. The optical signals are guided using the Transmission Structures to the Data Collector and further into the tissue through the hydrogel. Herein, numeral 19 refers to a Light shielding on PCB, numeral 20 refers to light shielding in gel, numeral 21 refers to LEDs, numeral 22 refers to photodiodes, and numeral 23 refers to amplifier circuits.

Figure 9:
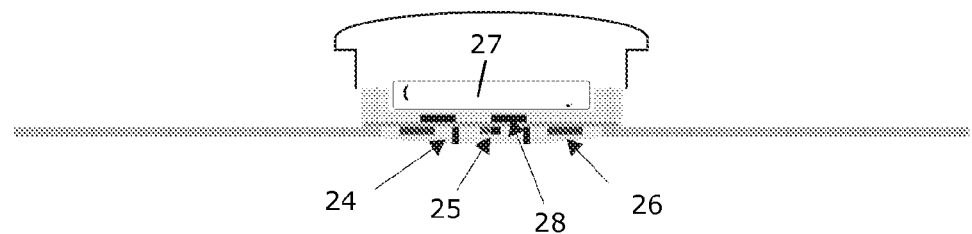

FIG. 9: The fig. illustrates a possible integration of the optical system and components in the monitoring device. The optical components are integrated as a part of the Data Collector. The Data Collector and Processor have electrical connections through the Transmission Structures by conduction silicon wires. Herein, numeral 24 refers to a light shielding, numeral 25 refers to LEDs, numeral 26 refers to photodiodes, numeral 27 refers to a coin cell battery, and numeral 28 refers to amplifier circuits.

The layout and geometry of optical sensor comprising electro optic components of light emitting diodes (LEDs) and photodiodes is seen in FIG. 3. The geometry and separation between the LEDs and photodiodes is essential as this influences the quality of measured photoplethysmograms (PPGs). Preferably, the separation between the LEDs and photodiodes should be in the range 4 mm to 7 mm.

Figure 10:
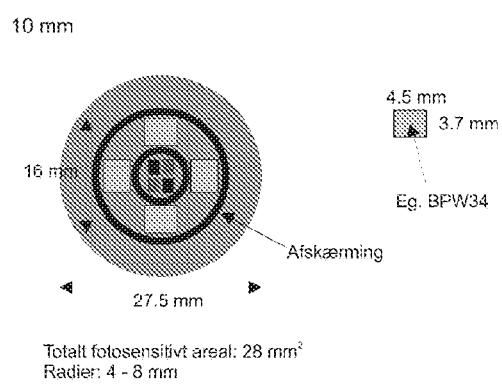
Figure 10:
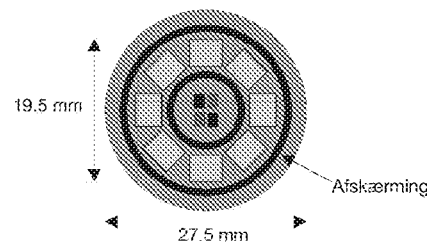

FIG. 10: The fig. shows the top view of two layouts of a printed circuit board with electro optic components of light emitting diodes (LEDs) and photodiodes. 4-8 photodiodes are mounted in an annular geometry with (LEDs) in the centre. The wavelengths of the LEDs are 660 nm and 940 nm, respectively. The photodiodes are e.g. the BPW34 or similar. Herein, numeral 29 and 30 refer to shielding.

The device may comprise one or more of the following components:
Photodiodes
  High quantum efficiency in the range 390 nm to 1100 nm.
  Low capacitance per area i.e. max 1 $nF/cm^2$
  Surface mountable devices
  The photodiodes size should fit to a circle with a radius of 4 mm to 6 mm from the center to the first edge of the photodiodes
  The photodiodes should preferably have an antireflection coating matched to the refractive index of the gel.
Light emitting diodes
  To or more wavelengths in the range 390 nm to 1100 nm, preferably 660 nm and 940 nm
  Low optical noise
  Surface mountable devices.
  Small form factor approx. 1 mm by 2 mm.
Gels
  Transparent, e.g. 50% or more of the light with wavelengths in the range 390 nm to 1100 nm is transmitted per mm gel.
  Refractive index of in the range of 1.01 to 1.7 (The refractive index of in vivo tissue is in the range 1.34-1.42 is as disclosed in Tearney, G. J. et al. "Determination of the refractive index of highly scattering human tissue by optical coherence tomography", Opt Lett, 1995, 20, 2258 and Ding, H. et al. "Refractive indices of human skin tissues at eight wavelengths and estimated dispersion relations between 300 and 1600 nm." Phys Med Biol, vol. 51, no. 6, pp. 1479-1489, March 2006.)
  Non-conducting gel; if the gel is in contact with conducting parts of the printed circuit board.
  Conduction gel if used for electrical contact to the skin.
Amplifier
  If a general trans-impedance amplifier is used it should have the following specifications:
  The bandwidth should be compatible with simultaneous measurements of a 120 Hz sinusoidal oscillating background light, red PPG, and infrared PPG. E.g. if the signals should be sampled within a maximum of 1% change of the background light normalized with respect to the maximum they should be sampled within 26 μs. It is possible to have a shorter bandwidth if the sampling frequency is higher than 240 Hz (Nyquist criterion). The background light signal can then be interpolated. The bandwidth should further be compatible with a desired rise time for the photodiodes and amplifier circuit. The rise time represents excess power consumption by the LEDs. E.g. the sampling time of the MSP430 is 4 μs. If an excess power consumption of the LEDs due to the rise time is 1% then the rise time should be 40 ns, equivalent to a bandwidth of the amplifier of 8.75 MHz. The CC2430 has a sampling frequency of 160 μs, applying the same requirement gives a bandwidth of 218 kHz.
  The operational amplifier should have a low noise. In particular the flicker noise should be low since the flicker noise is likely to be in the same band as the PPG signal.
  The gain/noise ratio should be as high as possible and likely higher than 109.
Alternatively a switched integrated trans-impedance amplifier can be use to reduce noise by integrating the signal over a time window.

The invention claimed is:

1. A monitoring device suitable for attachment to a surface of a subject, the device comprising: a data collector and a processor, the data collector having a lower surface, adapted for adhesive contact with a skin surface of the subject and adapted for receiving a physiological signal from the surface, the data collector comprising a transmission structure for transmitting a monitoring signal which represents the physiological signal to the processor, and the processor being detachably attachable to an upper surface of the data collector and comprising a connection structure which, upon attachment, connects to the transmission structure for receiving the monitoring signal from the data collector, wherein the processor comprises an electronic circuit for processing the monitoring signal to provide monitoring data which relates to a physiological state of the subject, wherein at least one of the data collector and the processor comprises a transducer which can convert the physiological signal to a data signal which can be processed electronically, wherein the data collector comprises a base forming the lower surface and an opposite upper surface, the data collector further comprising an adapter projecting in an upwards direction from the upper surface and forming an anchoring structure cooperating with a gripping structure on the processor for the detachable attachment of the processor to the data collector and wherein the gripping structure is adapted to destroy the anchoring structure upon detachment of the data collector from the processor.

2. The device according to claim 1, wherein the connection structure and transmission structure are adapted to transfer electrical signals.

3. The device according to claim 1, wherein the connection structure and transmission structure are adapted to transfer optical signals.

4. The device according to claim 1, wherein the base and adapter have different shapes.

5. The device according to claim 1, wherein the base is more elastically deformable than the adapter.

6. The device according to claim 1, wherein the transmission structure comprises at least two individual transmitters for transmitting separate data signals from the base through the adapter to the processor.

7. The device according to claim 6, wherein the transmitters are individually and movably suspended in a body of an electrically isolating material.

8. The device according to claim 7, wherein the body forms a seat for a battery, wherein the transmitters are arranged along a line extending circumferentially about the battery.

9. The device according to claim 8, wherein the seat includes an electrically conductive bushing extending circumferentially about the battery.

10. The device according to claim 1, further comprising an actuator which converts energy from one form to another form which can be sensed by an individual using the device.

11. The device according to claim 10, wherein the actuator is included in the data collector.

12. The device according to claim 11, wherein the data collector is adapted for two-way communication of signals to and from an individual using the device.

13. The device according to claim 1, wherein the lower surface comprises an adhesive with a refractive index in the range of 1.01 to 1.45.

14. A method of monitoring data based on physiological signals received from a subject, the method comprising attaching a data collector capable of detecting physiological signals to a surface of the subject and using a separate processor which is attached to the data collector for processing the detected signals and to provide monitoring data which relates to a physiological state of the subject, wherein at least one of the data collector and the processor comprises a transducer which can convert the physiological signal to a data signal which can be processed electronically, wherein the data collector is attached to the processor by use of an anchoring structure cooperating with a gripping structure on the processor, wherein the gripping structure destroys the anchoring structure upon detachment of the data collector from the processor.

* * * * *